United States Patent [19]

Mitchell et al.

[11] Patent Number: 4,805,413
[45] Date of Patent: Feb. 21, 1989

[54] PROCESS FOR CRYOGENICALLY SEPARATING NATURAL GAS STREAMS

[75] Inventors: E. Keith Mitchell, Shawnee; Donald N. Reed, Edmond, both of Okla.

[73] Assignee: Kerr-McGee Corporation, Oklahoma City, Okla.

[21] Appl. No.: 166,445

[22] Filed: Mar. 10, 1988

[51] Int. Cl.$^4$ .............................................. F25J 3/02
[52] U.S. Cl. .......................................... 62/24; 62/31; 62/39; 62/42
[58] Field of Search .................. 62/23, 24, 31, 32, 38, 62/39, 42

[56] References Cited

U.S. PATENT DOCUMENTS

| | | | |
|---|---|---|---|
| 4,203,741 | 5/1980 | Bellinger et al. | 62/23 |
| 4,256,476 | 3/1981 | Van Baush | 62/23 |
| 4,504,295 | 3/1985 | Davis et al. | 62/30 |
| 4,711,651 | 12/1987 | Sharma | 62/24 |

OTHER PUBLICATIONS

"Integrated Nitrogen Rejection Facility Produces Fuel and Recovers NGL's", *Energy Progress*, vol. 4, No. 4, Dec. 1984, pp. 214–221, by S. K. Looney, B. C. Price and C. A. Wilson, Arco Oil.

*Chemical Engineers' Handbook*, John H. Perry, Section 12, pp. 29–30, 4th Ed. (1963).

*Primary Examiner*—Ronald C. Capossela
*Attorney, Agent, or Firm*—William G. Addison; John P. Ward

[57] ABSTRACT

The present invention relates to an improved process for the recovery, individually, of natural gas liquids methane and nitrogen from a gaseous feed stream such as natural gas without the need for auxiliary refrigeration and without or with only minimal need for supplemental compressor or pumping equipment. The gaseous feed stream is separated in multiple steps utilizing process-derived streams and minimal pressure reductions to achieve and provide the refrigeration requirements necessary to effect the separation.

23 Claims, 1 Drawing Sheet

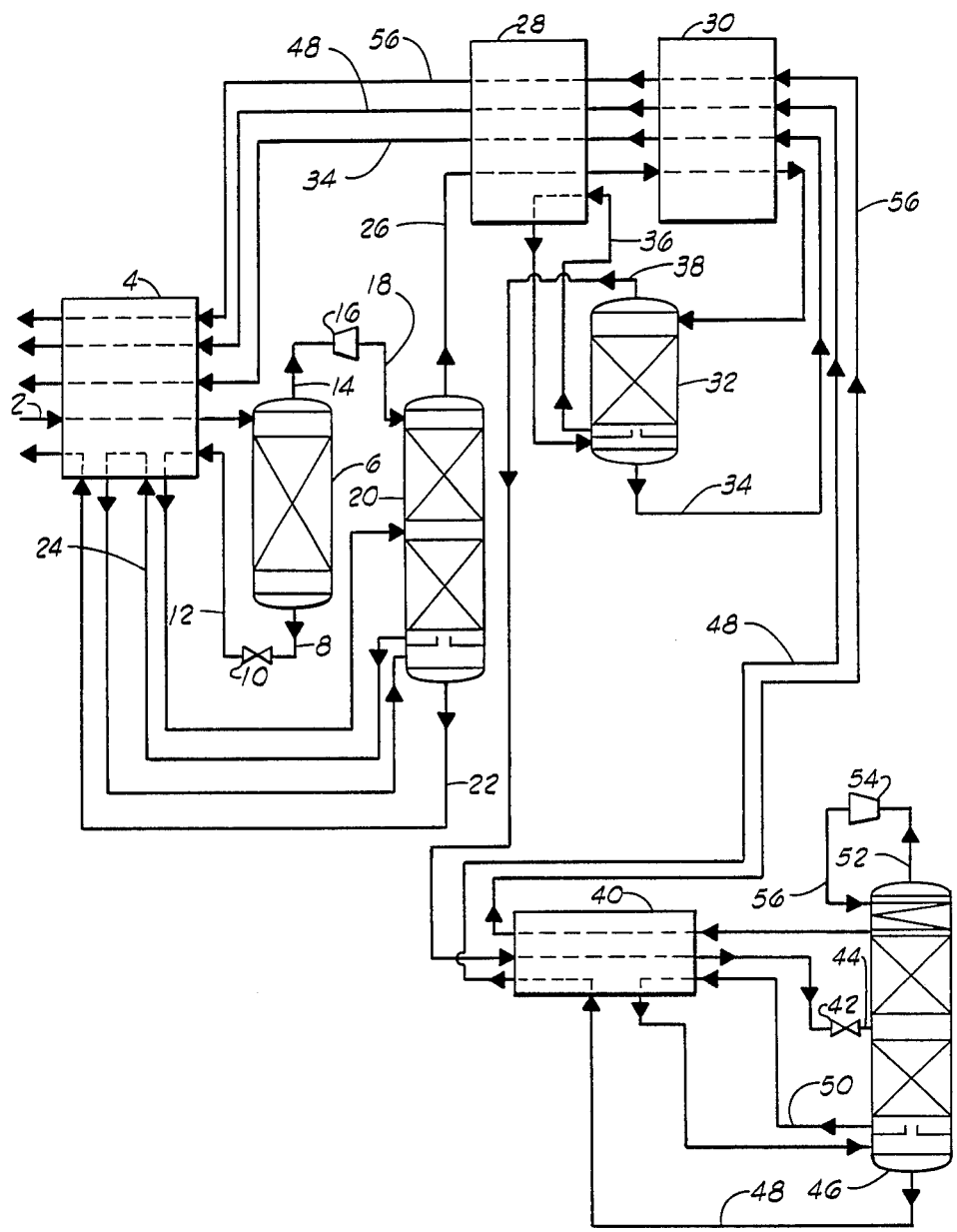

PROCESS FOR CRYOGENICALLY SEPARATING NATURAL GAS STREAMS

CROSS-REFERENCE TO RELATED APPLICATIONS

Aspects of the present invention are related to subject matter disclosed in co-pending Application Ser. No. 46,316 entitled "Process For Recovering Helium From A Natural Gas Stream" filed May 6, 1987 and assigned to the assignee of the present invention.

FIELD OF THE INVENTION

The present invention relates to an improved process for cryogenically separating gaseous streams such as natural gas streams. More particularly, the present invention relates to an improved process for cryogenically separating and recovering the various constituents in natural gases wherein the cryogenic temperatures required to accomplish the separation are attained solely through autorefrigeration and indirect heat exchange using process-derived streams.

BACKGROUND OF THE INVENTION

The separation of natural gas streams by processes based upon the use of cryogenic techniques is known. Such processes basically consist of subjecting the natural gas stream to be separated to successively lower temperatures whereby the natural gas stream is separated or fractionated into its component parts in accordance with the boiling points of the various components. These components generally include, in descending order of their boiling points, hydrocarbons heavier than methane such as ethane and heavier hydrocarbon components, methane itself and nitrogen.

In general, most known natural gas separation processes comprise at least three distinct operative steps or stages. These include (1) a preliminary gas treatment step for the removal of water and acidic gases such as carbon dioxide and hydrogen sulfide, (2) a natural gas liquids product separation step using low but noncryogenic temperatures for the separation and recovery of the ethane and heavier hydrocarbon components and (3) a nitrogen separation or rejection step employing cryogenic temperatures for the separation and recovery of a methane-rich product stream useful as a high BTU content fuel source.

A typical natural gas treatment process is disclosed in U.S. Pat. No. 4,504,295. In this patent, a process is described which is directed to the separation of natural gas streams into a natural gas liquid product stream, a methane-rich product stream and a nitrogen-rich product or waste gas stream. The principal characteristic of the patented process is said to be the ability to effect the critical low temperature (i.e., cryogenic) separation at high pressures in a single high pressure distillation column. The refrigeration required to attain the cryogenic temperatures necessary to effect the critical separation at high pressures is provided by an auxiliary closed loop heat pumped refrigerant such as methane. This refrigerant is employed in indirect heat exchange relationship to various reflux and reboil streams flowing to and from the high pressure distillation column. According to the patent, the process provides the ability to deliver methane-rich and nitrogen-rich product streams at high pressures, thus avoiding the need for the supplemental compressor or pumping equipment required in more conventional low pressure processes.

In the more conventional low pressure processes, the low temperature refrigeration required for the critical separation is provided, at least in part, by expansion (i.e., use of the Joule-Thomson cycle) of the feed gas stream and/or various intermediate streams generated by such processes. As a result of using expansion, the final separation of the feed gas stream into methane-rich and nitrogen-rich product streams is carried out at or near atmospheric pressure. Being at or near atmospheric pressure, these product streams or at least the methane-rich product stream must be recompressed to pipeline or transportation pressures.

Illustrative of one such low pressure process for the separation of natural gas streams is the integrated process described in *Energy Progress*, Vol. 4, No. 4, December 1984, pp 214–221. In that process, the final critical separation of the natural gas stream, substantially free of its natural gas liquid constituents, into a methane-rich product stream and a nitrogen-rich product (or waste gas) stream is carried out in a low pressure distillation vessel operated at or near atmospheric pressure. The refrigeration required to effect the separation is provided by both indirect heat exchange and expansion of the intermediate product streams recovered from a high pressure distillation column operated immediately upstream of the low pressure column to effect a rough methane/nitrogen split. Finally, the separated and recovered methane-rich product stream is recompressed, by means of compressors or pumps, to elevated pressures.

The above references describe processes representing the extremes of known natural gas separation processes. It is clear that a process wherein neither auxiliary refrigeration nor supplemental compressor or pumping equipment is required would represent an advancement in the art.

SUMMARY OF THE INVENTION

It now has been discovered that gaseous streams containing nitrogen, methane and ethane and heavier hydrocarbon constituents can be cryogenically separated without the need for auxiliary cryogenic refrigeration and without or, at best, with only minimal need for supplemental compressor or pumping equipment.

In accordance with this discovery, the present invention provides a process for the separation of a gaseous stream containing nitrogen, methane and ethane and heavier hydrocarbon constituents into at least four distinct process-derived product streams. These distinct product streams include a natural gas liquids product stream, a first and a second methane-rich liquid product stream and a substantially pure nitrogen gas stream. The present invention utilizes both indirect heat exchange employing the above disclosed process-derived product streams and expansion as the sole means for achieving the cryogenic temperatures required in certain of the separation steps encompassed by the process.

Broadly, the process of the present invention comprises a series of manipulative steps or stages for the removal and recovery of the various constituents contained in a gaseous feed stream. Specifically, the process of this invention consists of first cooling a gaseous feed stream such as a natural gas stream containing nitrogen, methane and ethane and heavier hydrocarbon constituents by means of indirect heat exchange with one or more of the above described process-derived product streams or combinations of one or more of said product streams with a noncryogenic heat exchange refrigerant medium. This cooling effects a condensation, under noncryogenic temperature conditions, of at least a portion of the methane and a substantial portion of the ethane and heavier hydrocarbon constituents contained in the gaseous feed stream. The cooled, partially condensed gaseous feed stream is separated into a first liquid effluent stream and a first vapor phase stream.

The first vapor phase stream is further cooled by either indirect heat exchange with one or more of the above disclosed process-derived product streams, expansion, or a combination thereof, to temperatures extending down into the cryogenic range (i.e., temperatures of minus 100° C. and below). This cooled first vapor phase stream and the first liquid effluent stream then are commingled and subsequently separated into an ethane-rich liquid product stream and a methane-rich vapor phase stream. The ethane-rich liquid product stream is comprised of a condensed minor portion of the methane and a condensed substantially major portion of the ethane and heavier hydrocarbon constituents present in the initial gaseous feed stream. The methane-rich vapor stream is comprised of the nitrogen, the non-condensed major portion of the methane and the non-condensed, substantially minor portion of the ethane and heavier hydrocarbon constituents present in the initial gaseous feed stream.

The ethane-rich liquid product stream is recovered and the methane-rich vapor phase stream is subjected to further cooling within the cryogenic range of temperatures by indirect heat exchange with one or more of the above disclosed process-derived product streams to effect a further condensation of a substantial portion of the noncondensed major portion of the methane and the noncondensed substantially minor portion of the ethane and heavier hydrocarbon constituents. The further cooled and condensed methane-rich vapor phase stream then is separated into a first methane-rich liquid product stream and a nitrogen-rich vapor stream. The first methane-rich liquid product stream, which comprises a minor portion of the nitrogen, a condensed substantial portion of the noncondensed methane and the condensed balance of the noncondensed ethane and heavier hydrocarbon constituents present in the methane-rich vapor phase stream, is recovered.

In a final step of the process of the present invention, the nitrogen-rich vapor stream, comprised of nitrogen and a remaining noncondensed minor portion of the methane, is further cooled within the cryogenic range of temperatures by indirect heat exchange utilizing one or more of the above described process-derived streams and expansion to condense the remaining noncondensed minor portion of the methane. This cooled and condensed nitrogen-rich vapor stream then is subjected to separation to remove therefrom a substantially pure nitrogen gas stream and provide a second methane-rich liquid product stream.

DESCRIPTION OF THE DRAWING

The single Figure is a schematic view illustrating the general flow scheme of the process of the present invention.

DETAILED DESCRIPTION OF THE INVENTION

With reference to the single Figure, the present invention consists of an improved process for cryogenically separating and recovering gaseous feed streams containing nitrogen, methane and ethane and heavier hydrocarbon constituents into various useful product streams. The process of the present invention allows for such separation and recovery without the need for auxiliary refrigeration and without the need or with only the minimal need for supplemental compressor or pumping equipment.

In accordance with the improved process of the present invention, an initial gaseous feed stream such as a natural gas stream containing from about 5 to about 95 volume percent of nitrogen, the remainder being hydrocarbon constituents of which up to about 30 volume percent is ethane and heavier hydrocarbon constituents, with the balance being methane, is received at an elevated temperature ranging from about 10° C. to about 50° C. and at an elevated pressure ranging from about 400 pounds per square inch gauge (psig) (28.1 kg/sq cm) to about 4000 psig (281 kg/sq cm). This initial gaseous feed stream is pretreated (by means not shown) to remove any water, carbon dioxide and hydrogen sulfide contained therein and conveyed via a conduit 2 through an indirect heat exchange zone 4 to a first fractionation zone 6.

Within indirect heat exchange zone 4, which can comprise one or more indirect heat exchange means such as, for example, shell and tube and plate-type heat exchangers and the like, the pretreated gaseous feed stream is brought into indirect heat exchange contact with one or more heat exchange media. The heat exchange media which can be employed within indirect heat exchange zone 4 will consist, in the main, of one or more of the above mentioned process-derived product streams. Again, these streams include the ethane-rich liquid product stream, both the first and second methane-rich liquid product streams and the substantially pure nitrogen gas stream. Furthermore, combinations of these process-derived product streams with other heat exchange medium (e.g., propane) provided by use of auxiliary, noncryogenic refrigeration means (not shown) can be employed. Other process-derived streams, disclosed and described hereinbelow, also may be employed as heat exchange media within indirect heat exchange zone 4.

As the pretreated gaseous feed stream is conveyed via conduit 2 through indirect heat exchange zone 4 it is cooled to a temperature sufficient to effect a condensation of at least a portion of the methane and a major portion of the condensable ethane and heavier hydrocarbon constituents (such as, for example, propane, butane, isobutane, pentane, isopentane, and the like) contained in the gaseous feed stream. Temperatures sufficient to effect the condensation are the temperatures in the range of from about minus 20° C. to about minus 120° C.

The cooled, gaseous feed stream is introduced into first fractionation zone 6 which may comprise one or more conventional packed or plate towers, or simple flash towers for flash chambers. The cooled stream is separated within said first fractionation zone 6 into a first liquid effluent stream comprising the condensed portions of the methane, ethane and heavier hydrocarbon constituents and a first vapor phase stream comprised of nitrogen and the balance of the noncondensed methane and the noncondensed ethane and heavier hydrocarbon constituents. Depending upon the pressure of the gaseous feed stream and the temperature to which it is cooled, the first liquid effluent stream will contain from about 1.0 to about 75 volume percent of the methane and from about 40 to about 99 volume percent of the ethane and heavier hydrocarbon constituents present in the gaseous feed stream. The noncondensed constituents contained in the first vapor phase stream will include all of the nitrogen, from about 25 to about 99 volume percent of the methane and from about 1 to about 60 volume percent of the ethane and heavier hydrocarbon constituents. The percentages are based on the unit volume of each of these components present in the gaseous feed stream.

The first liquid effluent stream and the first vapor phase stream are withdrawn from the first fractionation zone 6 by a conduit 8 and a conduit 14, respectively. The first liquid effluent stream is conveyed via the conduit 8, a throttle valve 10 and a conduit 12 to an intermediate section of a second fractionation zone 20. As shown on the drawing, the conduit 12 passes through the indirect heat exchange zone 4 and in heat exchange proximity to the conduit 2 to effect heat exchange between the warmer, initial gaseous feed stream flowing in conduit 2 and the cooler first liquid effluent stream flowing through conduit 12. In this manner, a portion of the heat necessary for the separation to be performed in the second fractionation zone 20 is provided by the incoming initial gaseous feed stream while a portion of the refrigeration necessary to effect the desired partial condensation of the initial gaseous feed stream is provided by the first liquid effluent stream.

The first vapor phase stream is conveyed through the conduit 14, an expansion zone 16 and a conduit 18 to an upper section of the second fractionation zone 20. The conveyance of the first vaporous phase stream through the expansion zone 16 effects a reduction in the pressure of this first vapor phase stream down to a value within the range of from about 125 psig (8.8 kg/sq cm) to about 600 psig (42.2 kg/sq cm). This reduction in pressure also causes a concomitant reduction in the temperature of the first vapor phase stream to a temperature in the range of from about minus 35° C. to about minus 130° C. which is the primary purpose of the expansion zone 16.

In an alternative embodiment, cooling of the first vapor phase stream can be accomplished by using an indirect heat exchange means (not shown) such as described hereinabove in place of the expansion zone 16 illustrated in the Figure. In this alternative embodiment, various process-derived streams such as the above mentioned first and second methane-rich liquid product streams and the substantially pure nitrogen gas stream can be employed as heat transfer media to cool the first vapor phase stream to temperatures within the range specified above. However, the preferred means for accomplishing this cooling is by way of the expansion zone 16 as illustrated in the single Figure. In general, the expansion zone 16 can comprise a conventional expansion engine of either the piston or turbine-type as briefly described in Perry's *Chemical Handbook*, Section 12, pages 29-30, 4th Ed. (1963) or simple throttle valve.

This reduction in temperature of the first vapor phase stream, either by reducing the pressure of said stream by means of the use of the expansion zone 16 as illustrated or by indirect heat exchange of said stream with one or more of the process-derived streams (not illustrated) causes condensation of further portions of the remaining balances of the methane and ethane and heavier hydrocarbon constituents. Specifically, said cooling leads to the condensation of from about 1.0 to about 85 volume percent of the remaining balance of the methane and from about 40 to 99 percent of the remaining balance of the ethane and heavier hydrocarbon constituents contained in the first vapor phase stream.

As disclosed hereinabove, subsequent to the cooling and condensation of the first vapor phase stream in the expansion zone 16, the first vapor phase stream is conveyed via the conduit 18 to the upper section of the second fractionation zone 20. This second fractionation zone 20 can comprise a single vessel or multiple vessels arranged and operated in series. Such vessel or vessels can all be of the same types as described for use in the first fractionation zone 6, i.e., conventional packed or plate-type towers or simple flash towers or chambers.

Within the second fractionation zone 20, the first liquid effluent and the cooled and condensed first vapor phase stream are commingled and subjected to fractionation conditions sufficient to produce an ethane-rich liquid product stream and a methane-rich vapor phase stream. The fractionation conditions employed within the second fractionation zone 20 include temperatures ranging from about plus 50° C. in the lower section thereof to about minus 130° C. in the upper section thereof and pressures ranging from about 125 (8.8 kg/sq cm) to about 600 psig (42.2 kg/sq cm).

As noted hereinabove, a portion of the heat necessary to achieve the above temperatures is obtained by conveying the first liquid effluent stream separated in first fractionation zone 6 from said zone 6 via the conduit 8, the throttle valve 10 and the conduit 12 and through the indirect heat exchange zone 4. Therein it is passed in indirect heat exchange proximity with the incoming gaseous feed stream flowing through conduit 2. The remainder of the heat necessary to achieve the above temperatures within the second fractionation zone 20 is provided by removal of a side stream of the ethane-rich liquid product stream collected in the lower section of the second fractionation zone 20. This side stream is withdrawn from the second fractionation zone 20 via a conduit 24 which is passed through the indirect heat exchange zone 4 and in heat exchange proximity to the conduit 2 and back to the first fractionation zone 20. As the side stream of the ethane-rich liquid product stream flows through the conduit 24 and in heat exchange proximity to the conduit 2 it is heated by indirect heat exchange with the incoming pretreated gaseous feed stream flowing through the conduit 2.

The ethane-rich liquid product stream produced within the second fractionation zone 20 is withdrawn therefrom by way of a conduit 22. In general, this ethane-rich liquid product stream will comprise a condensed minor portion of the methane and a condensed substantially major portion of the ethane and heavier hydrocarbon constituents present in the initial gaseous feed stream. Typically, this ethane-rich liquid product stream will comprise from about 0 to about 10 volume percent of the methane and, taken collectively, from about 40 to about 99 volume percent of the ethane ad heavier hydrocarbon constituents present in the gaseous feed stream undergoing separation.

In general, the methane-rich vapor phase stream withdrawn as overhead from the second fractionation zone 20 via a conduit 26 will be comprised of nitrogen, a noncondensed major portion of the methane and a noncondensed substantially minor portion of the ethane and heavier hydrocarbon constituents present in the initial gaseous feed stream. Typically, this methane-rich vapor phase stream will comprise from about 90 to about 100 volume percent of the nitrogen, from about 90 to about 100 volume percent of the methane and from about 1 to about 60 volume percent of the ethane and heavier hydrocarbon constituents present in said gaseous feed stream.

The above methane-rich vapor phase stream, withdrawn from the second fractionation zone 20 via the conduit 26, will be at a temperature ranging from about minus 35° C. to about minus 130° C. and under a pressure ranging from about 125 psig (8.8 kg/sq cm) to about 600 psig (42.2 kg/sq cm). This stream is conveyed by the conduit 26 through indirect heat exchange zones 28 and 30 wherein it further is cooled to temperatures in the range of from about minus 100° C. to about minus 155° C. Refrigeration is provided within the indirect heat exchange zones 28 and 30 utilizing the process-derived first and second methane-rich liquid product streams and the process-derived substantially pure nitrogen gas stream described hereinbelow as heat transfer media. These heat transfer media are passed through the indirect heat exchange zones 28 and 30 via conduits 34, 48 and 56, respectively. The cooling which occurs within the indirect heat exchange zones 28 and 30 effects a substantial condensation of he noncondensed major portion of the methane and the condensed balance of the noncondensed substantially minor portion of the ethane and heavier hydrocarbon constituents. In general, this cooling of the methane-rich vapor phase stream results in the condensation of from about 0 to about 10 volume percent of the nitrogen, from about 30 to about 80 volume percent of the noncondensed major portion of the methane and from about 99 to about 100 volume percent of the noncondensed substantially minor portion of the ethane and heavier hydrocarbon constituents present in this methane-rich vapor phase stream. The percentages given are based upon the unit volume of each component contained in the methane-rich vapor phase stream introduced into a third fractionation zone 32.

The cooled and condensed methane-rich vapor phase stream then is introduced into an upper section of the third fractionation zone 32. Again, like the second fractionation zone 20, this third fractionation zone 32 can comprise one or more conventional packed or plate-type towers or simple flash towers or chambers. Within the third fractionation separation zone 32, the cooled and condensed methane-rich vapor phase stream is separated into a first methane-rich liquid product stream and a nitrogen-rich vapor phase stream. The operating conditions employed within the third fractionation zone 32 include temperatures ranging from about minus 75° C. in a lower section thereof to about minus 155° C. in the upper section thereof and pressures ranging from about 125 psig (8.8 kg/sq cm) to about 600 psig (42.2 kg/sq cm). To further enhance the separation of the cooled and condensed methane-rich vapor phase stream in the third fractionation zone 32, a portion of a first methane-rich liquid product collected in a lower section of the third fractionation zone 32 is withdrawn therefrom via a conduit 36. This conduit 36 passes through indirect heat exchange zone 28 wherein it is located in indirect heat exchange proximity to conduit 26. As the sidestream of the first methane-rich liquid product is conveyed through the conduit 36 and passed in indirect heat exchange proximity to the conduit 26 within heat exchange zone 28, the first methane-rich liquid product stream is heated against the methane-rich vapor phase stream flowing through the conduit 26. The heated sidestream, which will range in temperature from about minus 75° C. to about minus 120° C., is returned to the lower section of the third fractionation zone 32 via conduit 36 wherein it causes reboiling of the first methane-rich liquid product. This reboiling enhances the separation between the methane and nitrogen contained in the cooled and condensed methane-rich vapor phase stream which is continuously introduced into the upper section of the third fractionation zone 32.

The first methane-rich liquid product produced in the third fractionation zone 32 is withdrawn as a product stream through a conduit 34. This liquid product stream generally comprises a minor portion of the nitrogen, a condensed substantial portion of the methane and the condensed balance of the ethane and heavier hydrocarbon constituents contained in the methane-rich vapor phase stream. Typically, this first methane-rich liquid product stream will contain from about 0 to about 10 volume percent of the nitrogen, from about 30 to about 80 volume percent of the methane and from about 99 to about 100 volume percent of the ethane and heavier hydrocarbon constituents present in the cooled and condensed methane-rich vapor phase stream introduced into the third fractionation zone 32.

The first methane-rich liquid product stream constitutes a process-derived stream suitable for use as an indirect heat exchange medium in the process of the present invention. Thus, prior to the removal of this product stream from the process train, it is passed back through the process in indirect heat exchange relationship with the initial gaseous feed stream as well as various other process generated intermediate streams undergoing treatment to extract from this product stream the refrigeration contained therein. In particular, and as illustrated in the single Figure, the first methane-rich liquid product stream is withdrawn from the third fractionation zone 32 via the conduit 34 and conveyed back through the indirect heat exchange zones 30, 28 and 4 wherein the refrigeration contained in this first methane-rich liquid product stream is recovered.

Also separated within the third fractionation zone 32 is a nitrogen-rich vapor phase stream. This stream, which comprises the major portion of the nitrogen, and the remaining minor portion of the noncondensed methane, is withdrawn from the third fractionation zone 32 by way of a conduit 38. Typically, this nitrogen-rich vapor phase stream will contain from about 90 to about 100 volume percent of the nitrogen, from about 20 to about 70 volume percent of the methane and from about 0 to about 1 volume percent of the ethane and heavier hydrocarbon constituents present in the cooled and condensed methane-rich vapor phase stream introduced into the third fractionation zone 32.

The above described nitrogen-rich vapor phase stream is conveyed via the conduit 38, through an indirect heat exchange zone 40, a throttle valve 42 and a conduit 44 to a fourth fractionation zone 46. Within the indirect heat exchange zone 40, which utilizes both the second methane-rich liquid produce stream and the substantially pure nitrogen gas stream described hereinbelow as heat transfer media (i.e., as refrigerants), the nitrogen-rich vapor phase stream is first cooled to a temperature in the range of from about minus 155° C. to about minus 195° C. This cooling of the nitrogen-rich vapor phase stream effects a condensation of the remaining minor portion of the noncondensed methane present in this vapor phase stream. This stream then is subjected to further cooling to temperatures in the range of from about minus 155° C. to about minus 195°

C. by reducing the pressure of this stream to a pressure ranging from about atmospheric pressure to about 200 psig (14.1 kg/sq cm) by means of a throttle valve 42. The cooled and reduced pressure vapor stream then is introduced by way of a conduit 44 into an intermediate section of the fourth fractionation zone 46. The fourth fractionation zone 46 also can comprise one or more vessels of the type or types disclosed hereinabove for use in any of the fractionation zones 6, 20 or 32. Thus, the type or types of vessels useful as the fourth fractionation zone 46 can include any of the aforementioned conventional packed or plate-type towers or simple flash towers or chambers.

Within the fourth fractionation zone 46, the cooled and reduced pressure nitrogen-rich vapor phase stream is separated into a second methane-rich liquid product stream and a substantially pure nitrogen gas stream. The second methane-rich liquid product stream comprises from about 0 to about 10 volume percent of the nitrogen and from about 90 to about 100 volume percent of the methane contained in the nitrogen-rich vapor phase stream introduced into the fourth fractionation zone 46. This second methane-rich liquid product stream is withdrawn from the fourth fractionation zone 46 via a conduit 48 and passed back through indirect heat exchange zones 40, 30, 28 and 4, respectively, prior to final recovery to provide a portion of the refrigeration requirements of the process of the present invention. This second methane-rich stream generally will be at a temperature of between about minus 75° C. and minus 130° C.

To further enhance the separation between the nitrogen and methane constituents contained in the nitrogen-rich vapor phase stream introduced through conduit 44 into the fourth fractionation zone 46, a portion of the second methane-rich liquid product collected in the lower section of the fourth fractionation zone 46 is removed therefrom. This portion is removed as a side stream through a conduit 50, passed through the indirect heat exchange zone 40 in indirect heat exchange proximity to the conduit 38 therein and returned to the fourth fractionation zone 46. Heat exchange is effected between the sidestream of the second methane-rich liquid product flowing through the conduit 50 and the nitrogen-rich vapor phase stream flowing through the conduit 38 within indirect heat exchange zone 40. This heat exchange results in a warming of the sidestream sufficient to provide the heat necessary to the separation within the fourth fractionation zone 46. Generally, the temperature of this warmed sidestream will range from about minus 75° C. to about minus 130° C.

Also recovered from the fourth fractionation zone 46 is an overhead stream of substantially pure nitrogen. This substantially pure nitrogen gas stream is withdrawn from the fourth fractionation zone 46 via a conduit 52. This substantially pure nitrogen gas stream, which contains from about 90 to about 99 volume percent of this nitrogen and from about 1 to about 10 volume percent of the methane contained in the nitrogen-rich vapor phase stream introduced into the fourth fractionation zone 46, is further cooled to a temperature in the range from about minus 155° C. to about minus 205° C. This further cooling is effected by expanding said substantially pure nitrogen gas stream in an expansion zone 54. The further cooled pure nitrogen gas stream is returned to and passed through an upper section of the fourth fractionation zone 46 by way of a conduit 56. The further cooled pure nitrogen gas stream flowing through the conduit 56 provides the necessary reflux in the upper section of the fourth fractionation zone 46 for effecting separation between the nitrogen and methane constituents contained in the nitrogen-rich vapor phase stream introduced to the zone 46. Finally, the conduit 56 is passed back through the indirect heat exchange zones 40, 30, 28 and 4, respectively, wherein the substantially pure nitrogen gas stream is employed as a heat transfer medium to provide a portion of the refrigerant needs of the process. This nitrogen stream, due to the very low levels of methane present therein, can be vented to the atmosphere, if desired.

The present invention as described hereinabove provides an energy efficient process for the separation of a gaseous feed stream and particularly, a natural gas stream into an ethane-rich liquid product stream, a methane-rich liquid product stream and a substantially pure nitrogen gas stream without the need for auxiliary refrigeration to generate the required cryogenic temperatures and without or with only a minimal need for supplemental compressor or pumping equipment. While the process constituting the present invention has been described in terms of what is believed to be the preferred embodiments, it is to be understood that changes and modifications can be made thereto without departing from the spirit and scope thereof.

We claim:

1. A process for cryogenically separating a gaseous feed stream containing nitrogen, methane and ethane and heavier hydrocarbons comprising:
   (a) cooling said feed stream by indirect heat exchange with at least one process-derived refrigerant stream to effect a partial condensation of said feed stream;
   (b) separating the cooled and partially condensed feed stream into a first liquid effluent stream and a first vapor phase stream;
   (c) further cooling the first vapor phase stream;
   (d) commingling the first liquid effluent stream and the further cooled first vapor phase stream and separating the commingled streams into an ethane-rich liquid product stream and a methane-rich vapor phase stream;
   (e) recovering the ethane-rich liquid product stream and the methane-rich vapor phase stream and further cooling and methane-rich vapor phase stream by means of indirect heat exchange with at least one process-derived refrigerant stream to effect a partial condensation of the methane-rich vapor stream;
   (f) separating the further cooled and partially condensed methane-rich vapor phase stream into a first methane-rich liquid product stream and a nitrogen-rich vapor phase stream;
   (g) recovering the first methane-rich liquid product stream and the nitrogen-rich vapor phase and further cooling the nitrogen-rich vapor phase stream by means of indirect heat exchange with at least one process-derived refrigerant stream to effect a partial condensation of the nitrogen-rich vapor phase stream;
   (h) reducing the pressure of said further cooled and condensed nitrogen-rich vapor phase stream and separating said stream into a substantially pure nitrogen gas stream and a methane-rich liquid product stream; and
   (i) recovering, individually, the substantially pure nitrogen gas stream and the second methane-rich liquid product stream.

2. The process of claim 1 wherein said gaseous feed stream is a natural gas stream comprised of from about 5 to about 95 volume percent of nitrogen, the remainder being hydrocarbons of which up to about 30 volume percent is ethane and heavier hydrocarbon constituents, the balance being methane.

3. The process of claim 2 wherein the natural gas stream is received at an elevated temperature ranging from about 10° C. to about 50° C. and at an elevated pressure ranging from about 400 psig (28.1 kg/sq cm) to about 4000 psig (281 kg/sq cm).

4. The process of claim 2 wherein the cooling of the natural gas stream effects a partial condensation of the natural gas stream to provide a first liquid effluent stream comprising from about 1 to about 75 volume percent of the methane and, taken collectively, from about 40 to about 99 volume percent of the ethane and heavier hydrocarbon constituents contained in the natural gas stream.

5. The process of claim 4 wherein the cooling of the natural gas stream to effect the partial condensation of the natural gas stream further provides the first vapor phase stream comprising 100 volume percent of the nitrogen, from about 25 to about 99 volume percent of the methane and from about 1 to about 60 volume percent of the ethane and heavier hydrocarbon constituents contained in the natural gas stream.

6. The process of claim 2 wherein the first vapor phase stream is further cooled by a reduction in pressure of the first vapor phase stream in an expansion zone.

7. The process of claim 6 wherein the expansion of the first vapor phase stream effects a cooling of the first vapor phase stream to a temperature ranging from about minus 35° C. to about minus 130° C.

8. The process of claim 6 wherein the expansion of the first vapor phase stream effects a reduction in pressure of said stream to a pressure ranging from about 125 psig (8.8 kg/sq cm) to about 600 psig (42.2 kg/sq cm).

9. The process of claim 6 wherein the expanding and cooling of the first vapor phase stream effects a condensation of from about 1 to about 85 volume percent of the methane and from about 40 to about 99 volume percent of the ethane and heavier hydrocarbon constituents contained in the first vapor phase stream.

10. The process of claim 2 wherein the commingled first liquid effluent stream and the further cooled first vapor phase stream are separated at temperatures ranging from about minus 130° C. to about plus 50° C. and at pressures ranging from about 125 psig (8.8 kg/sq cm) to about 600 psig (42.2 kg/sq cm).

11. The process of claim 2 wherein the ethane-rich product stream comprises a condensed minor portion of the methane and a condensed substantially major portion of the ethane and heavier hydrocarbon constituents contained in the natural gas stream.

12. The process of claim 11 wherein the ethane-rich product stream comprises from about 0 to about 10 volume percent of the methane and, taken collectively, from about 40 to about 99 volume percent of the ethane and heavier hydrocarbon constituents contained in the natural gas stream.

13. The process of claim 2 wherein the methane-rich vapor phase stream comprises nitrogen, a noncondensed major portion of the methane and a noncondensed substantially minor portion of the ethane and heavier hydrocarbon contained in the natural gas stream.

14. The process of claim 13 wherein the methane-rich vapor phase stream comprises from about 90 to about 100 volume percent of nitrogen, from about 90 to about 100 volume percent of the methane and from about 1 to about 60 volume percent of the ethane an heavier hydrocarbons contained in the natural gas stream.

15. The process of claim 2 wherein the methane-rich vapor phase stream is further cooled to a temperature of from about minus 100° C. to about minus 155° C. by indirect heat exchange with at least one process-derived refrigerant stream selected from the group consisting of the first methane-rich liquid product stream, the second methane-rich liquid product stream and the substantially pure nitrogen gas stream.

16. The process of claim 15 wherein the further cooling of the methane-rich vapor phase stream effects a condensation of a minor portion of the nitrogen, a substantial condensation of the noncondensed major portion of the methane and condensation of the balance of the noncondensed substantially minor portion of the ethane and heavier hydrocarbons contained in the methane-rich vapor phase stream.

17. The process of claim 16 wherein the further cooling of the methane-rich vapor phase stream effects condensation of from about 0 to about 10 volume percent of the nitrogen, from about 30 to about 80 volume percent of the methane and from about 99 to about 100 value percent of the ethane and heavier hydrocarbons contained in the methane-rich vapor phase stream.

18. The process of claim 2 wherein the separation and recovery of the first methane-rich liquid product stream is carried out at temperatures ranging from about minus 75° C. to about minus 155° C. and at pressures of from about 125 psig (8.8 kg/sq cm) to about 600 psig (42.2 kg/sq cm).

19. The process of claim 18 wherein the first methane-rich liquid product stream comprises from about 0 to about 10 volume percent of the nitrogen, from about 30 to about 80 volume percent of the methane and from about 99 to about 100 volume percent of the ethane and heavier hydrocarbons contained in the methane-rich vapor phase stream.

20. The process of claim 2 wherein the nitrogen-rich vapor phase stream comprises a remaining noncondensed major portion of the nitrogen and a remaining noncondensed minor portion of the methane.

21. The process of claim 20 wherein the nitrogen-rich vapor phase stream is cooled to a temperature of from about minus 155° C. to about minus 195° C. by indirect heat exchange with at least one process derived refrigerant stream selected from the group consisting of the substantially pure nitrogen gas stream and the second methane-rich liquid product stream.

22. The process of claim 21 wherein the nitrogen-rich vapor phase stream is further cooled to a temperature of from about minus 155° C. to about minus 195° C. by expansion to a pressure ranging from about atmospheric pressure to about 200 psig to effect a partial condensation of the nitrogen and condensation of the remaining noncondensed minor portion of the methane contained in the nitrogen-rich vapor phase stream.

23. The process of claim 2 wherein the substantially pure nitrogen gas stream comprises from about 90 to about 99 volume percent of the nitrogen and from about 1 to about 10 volume percent of the methane contained in the further cooled nitrogen-rich vapor phase stream and wherein the second methane-rich liquid product stream comprises from about 1 to about 10 volume percent of the nitrogen and from about 90 to about 99 volume percent of the methane contained in the further cooled nitrogen-rich vapor phase stream.

* * * * *